United States Patent [19] | [11] 4,267,170
Seawell | [45] May 12, 1981

[54] METHODS OF USING CHLAMYDIA VACCINE FOR PREVENTING AND TREATING BOVINE DISEASES

[76] Inventor: Albert C. Seawell, 1047 Carol Ave., Ripon, Wis. 54971

[21] Appl. No.: 73,004

[22] Filed: Sep. 6, 1979

[51] Int. Cl.³ .......... A61K 39/118
[52] U.S. Cl. .......... 424/88; 424/89; 424/92; 424/85
[58] Field of Search .......... 424/85-93

[56] References Cited

U.S. PATENT DOCUMENTS

| | | | |
|---|---|---|---|
| 2,324,646 | 7/1943 | Rake et al. | 424/89 |
| 2,355,676 | 8/1944 | Rake et al. | 424/89 |
| 2,415,234 | 2/1947 | Bunney et al. | 424/89 |
| 2,417,777 | 3/1947 | Nigg | 424/89 |
| 3,465,077 | 9/1969 | Baker | 424/89 |
| 3,577,525 | 5/1971 | Baker | 424/89 |
| 3,674,864 | 7/1972 | Angelucci | 424/89 |
| 3,927,209 | 12/1975 | Straub | 424/89 |
| 4,039,656 | 8/1977 | Straub | 424/89 |
| 4,049,794 | 9/1977 | Straub | 424/89 |
| 4,132,775 | 1/1979 | Volenec et al. | 424/89 |

OTHER PUBLICATIONS

Mitzel, Jr. et al., P.S.E.B.M. 135(3):944-946 (1970) Cross-Immunity Among Strains of *Chlamydia-psittaci.*

McKercher D. G. et al., JAVMA 163(7pt.2):889-891 (1973) Vaccination Against Epizootic Bovine Chlamydial Abortion.

Mitzel, Jr. et al., Am. J. Vet. Res., 38(9):1361-1364 (1977), Vaccination Against Feline Pneumonitis.

Mitzel, Jr. et al., Abstr. Ann. Mtg. Am. Soc. Microbiol. 76(1976) E55 Evaluation of Feline Chlamydial Pneumonitis Vaccine in Cats.

Schachter, J., Psittacosis (Ornithosis, Feline Pneumonitis and Other Infections with *Chlamydia psittaci)* Bird Hosts Zoonoses in Diseases Transmitted from Animals to Man, W. T. Hubbert, W. F. McCulloch, ed., pp. 369-381 (1974), pub. 1975.

Waldhalm, D. G. et al., Theriogenology 11(6), (1979):441-444 Pathogenicity of *Chlamydia psittaci* After Serial Passage in Chicken Embryos.

Sayed H., Can. J. Microbiol. 22(7), 1976: 937-941 Differences in Physilochemical and Antigenic Properties of Chlamydial Strains.

England, J. J., Color. State U. Clinical Science Newsletter 3(2): 9-11 Mar.-Apr. 1980, Chlamydial Diseases of Domestic Animals.

Storz, J. et al., Int. J. Sys. Bact. 21:332, 1971, Tayonomy of the Chlamydiae: Reasons for Classifying Organisms of the Genes Chlamydia Family Chlamydiaceae in a Separate Order Chlamydiales Ord. Nov.

Buxton et al., Animal Microbiology, vol. 2 (1977), Blackwell Sci. Pub. Ltd., pp. 358A-364, 377-388, "Chlamydiae" (Miyagawanella, Bedsonia, PLV).

Stedman's Medical Dictionary, 23rd ed., Williams & Wilkins, Balt., MD, p. 263, "Chlamydia"-*Psittaci, Chlamydiaceae.*

*Primary Examiner*—Shep K. Rose
*Attorney, Agent, or Firm*—James E. Nilles

[57] ABSTRACT

Method of using a modified live Chlamydia-chicken embryo origin vaccine for prevention and treatment of disease processes creating or induced by Chlamydia organisms in aminals of the bovine species.

17 Claims, No Drawings

METHODS OF USING CHLAMYDIA VACCINE FOR PREVENTING AND TREATING BOVINE DISEASES

BACKGROUND OF THE INVENTION

1. Field of Use .

This invention relates generally to vaccines for veterinary use. In particular, it relates to Chlamydia vaccines useful for prevention and treatment of disease processes created or induced by Chlamydia organisms in mammalians other than felines, particularly those of the bovine species, and to methods for immunizing and treating such animals with such vaccines.

2. Description of the Prior Art

Various strains of the *Chlamydia psittaci* organism (psittacosis-lymphogranuloma group) have been reported frequently as involved in various mammalian and avian disease processes. The pathology described includes the following disease processes: enzootic abortion in ewes, epizootic bovine abortion, feline pneumonitis, psittacosis-ornithosis, sporadic bovine encephalomyelitis, transmissible serositis in sheep, calves and swine, bovine respiratory disease complexes, enzootic pneumonia in calves, neonatal diarrhea of calves, polyarthritis in sheep and others.

The "Merck Veterinary Manual", Fourth Edition, published by Merck & Co., Inc. of Rahway, N.J., U.S.A. (1973) provides specific descriptions of the aforementioned and other related pathologies, the occurrence of Chlamydial organisms in connection therewith, the recommended forms of treatment, and the chemotherapeutical agents known and recommended for use therewith, especially at pages 166, 272, 274, 277, 322, 375, 385 and 879, as well as elsewhere.

The following references designated numbers 1 through 16 provide further information about such diseases and their treatment.

1. Boidin, A. G., Cordy, D. R., and Adler, H. E.: A Pleuropneumonia-like Organism and a Virus in Ovine Pneumonia in California. Cornell Vet., 48, (1959): 410–430.

2. Edward, A. G., Mills, G. D., and Calhoon, J. R.: Production of Colostrum-Deprived Specific Pathogen-Free Calves. Lab. Anim. Care, 17, (1967): 103–109.

3. Eugster, A. K., and Storz, J.: Pathogenetic Events in Intestinal Chlamydial Infections Leading to Polyarthritis in Calves. J. Infect. Dis., 123, (1971): 41–50.

4. Gimenez, D. F.: Staining Rickettsiae in Yolk-Sac Cultures. Stain Technol., 39, (1964): 135–140.

5. Kawakami, Y., Omori, T., Fukuhara, S., Tokuda, G., Ishii, S., and Matumoto, M.: Studies on the Disease of Cattle Caused by a Psittacosis-Lymphogranuloma Group Virus (Miyagawanella). VII. Isolation of a Virus, Identified as a Member of the Psittacosis-Lymphogranuloma Group of Viruses, from Feces of Cattle. Jap. J. Exptl. Med., 25, (1955): 51–63.

6. Page, L. A.: Proposal for the Recognition of Two Species in the Genus Chlamydia Jones, Rake and Stearns, 1945. Internat. J. Sys. Bact., 18, (1968): 51–66.

7. Reed, C. J., and Muench, M.: A Simple Method for Estimation of Fifty Percent Endpoints. Am. J. Hyg., 27, (1938): 493–497.

8. Smith, P. C., Cutlip, R. C., and Page, L. A.: Pathogenicity of a Strain of *Chlamydia psittaci* of Bovine Intestinal Origin for Neonatal Calves. Am. J. Vet. Res., 34, (May, 1973): In press.

9. Storz, J., Collier, J. R., Eugster, A. K., and Altera, K. P.: Intestinal Bacterial Changes in Chlamydia-induced Primary Enteritis of Newborn Calves. Ann. New York Acad. Sci., 176, (1971): 162–175.

10. Storz, J., Eugster, A. K., Altera, K. P., and Olander, H. J.: Behavior of Different Bovine Chlamydial Agents in Newborn Calves. J. Comp. Path. & Therap., 81, (1971): 299–307.

11. Storz, J., Marriott, M. E., and Winterer, B. I.: Detection and Separation of Simultaneous Enterovirus and Intestinal Chlamydial Infection of Calves. Zentralbl. Bakt. (Orig.), 210, (1969): 75–81.

12. York, C. J., and Baker, J. A. A New Member of the Psittacosis-Lymphogranuloma Group of Viruses that Causes Infection in Calves. J. Exptl. Med., 93, (1951): 587–604.

13. York, C. J., and Baker, J. A.: *Miyagawanella bovis* Infection in Calves. Ann. New York Acad. Sci., 66, (1956): 210–214.

14. Journal of the South African Vet Association (1977), Vol. 48, p. 261. It mentions that "abortions in sheep and cattle is well controlled by vaccination, but as yet no effective vaccine for the protection of the newborn has been developed".

15. Deutsche Tieranztlicke Wochenschrift (1975), Vol. 82, pp. 221 It states that two inactivated vaccines—"were tested on 16,581 sheep. The effectiveness of immediate vaccination of pregnant, including aborting animals, was therefore proved for both vaccines".

16. Journal of the AVMA (1974), Vol. 165, No. 8, pp. 689 It describes the use (or refers to the use) of an inactivated vaccine.

Heretofore, the above-referred to disease processes have been treated in a conventional manner by means of chemotherapeutic agents, with particular success experienced by the use of high levels of tetracyclines orally or intravenously administered over prolonged periods of time. However, insofar as applicant is aware, there is no known vaccine which is commercially available for the prevention or treatment of these disease processes in any species of animal, other than in felines and particularly, there is no teaching or recommendation to use live or modified live vaccine in bovines.

An example of a commercially available vaccine for immunization against and prevention of feline pneumonitis is Feline Pneumonitis Vaccine, Modified Live Chlamydia-Chicken Embryo Origin (trade name PSITTACOID) produced for veterinary use only under U.S. Veterinary License No. 195-A for immunization of cats against Chlamydia psittaci by Fromm Laboratories, Inc., Grafton, Wisc. 53024, U.S.A. The recommended dosage and administration for cats is as follows: Rehydrate each 1 cc vial of vaccine with 1 cc of diluent and inject intramuscularly or subcutaneously. Vaccinate healthy cats of any age with one dose except that if the animal is less than 12 weeks of age a second dose should be given at 12 to 16 weeks of age. Annual revaccination with a single dose is recommended. Each 1 cc vial of vaccine contains the vaccine in desiccated form containing $10^{5.1}$ (at least 100,000 plus) modified live organisms which is to be diluted with a sterile diluent such as distilled water.

The aforementioned conventional treatment of bovines, for example, suffering from Chlamydial infections by means of chemotherapeutical agents is generally satisfactory, but has the drawbacks of being relatively time-consuming, expensive, and lacking long-term effectiveness. For example, the conventional treatment of an individual animal typically involves administration of recommended dosages of tetracyclines over a period of five or more consecutive days followed by subsequent observations at less frequent intervals to ascertain treatment effectiveness. Furthermore, a successfully treated individual animal remains a carrier of the disease organism and is itself susceptible to reoccurrence of the disease, as well as being a source of infection to other animals in the herd. Such treatment, therefore, is costly from the standpoint of veterinary services required and as regards the type and quantity of medication.

While the foregoing factors generally point to the desirability of discovering a more economical and effective control regime for Chlamydial infections in agricultural animals, particularly of those of the bovine species, none has heretofore been forthcoming for a variety of reasons. For example, historical experience and classical theory in the science and practice of veterinary medicine indicates that immunizing agents and methods of treatment involving the same may be successfully employed with one species of animal but are not necessarily effective, safe, or even available for another species. Indeed, not infrequently, whereas beneficial results may occur in one species, unpredictable detrimental results can and often do occur in others. This fact has led to the development of different points of view and schools of thought within the profession regarding the desirability and possible effectiveness of using specific agents on different species. Furthermore, it is very often not possible to perform any studies, experiments or tests to establish effectiveness or non-effectiveness, especially those involving large numbers of costly agricultural animals such as beef or dairy cattle, where the possibility of risk or failure may not only be costly and inconclusive, but totally disastrous.

SUMMARY OF THE INVENTION

Applicant reasoned that vaccination would provide more medical effectiveness in that it would prevent occurrence of the diseases and also operate as a form of therapy after onset of the disease. Applicant discovered that the aforementioned Feline Pneumonitis Vaccine can be used to treat dairy cattle known to be infected with the chlamydial organisms, and can also be used to treat new born calves to prevent the disease as well as to treat the inherited (congenital) from thereof.

Thus, applicant discovered that a chlamydia vaccine can be administered to, although not so limited, the bovine species to prevent, inhibit and lessen the severity of Chlamydial infections. More particularly, applicant has found that the Feline Pneumonitis Vaccine is useful for prevention and treatment of disease processes created or induced by the Chlamydia organisms in larger animals, especially those of the bovine species. The vaccine may be administered in specified dosages at specific intervals of time.

The route of administration is preferably parenteral. While not so limited, it has been found preferably to use deep intramuscular injection of 1 ml of commercially available Feline Pneumonitis Vaccine, Modified Live Chlamydia-Chicken Embryo Origin (containing $10^{5.1}$ modified live organism per 1 ml of desiccated vaccine), (trade name PSITTACOID), manufactured by Fromm Laboratories, Inc., Grafton, Wisc. 53024, U.S.A., U.S. Veterinary License No. 195-A, dissolved in 1 cc of sterile diluent such as distilled water. Insofar as is known, the Chlamydia organism is capable of producing interfon antibodies which means antibody protection is stimulated at the cell level at the point of challenge. It is also possible to produce localized antibodies in the respiratory system of bovines and other species if given as a nasal spray since this is a direct way to reach the respiratory system.

The schedule of vaccination is, but not limited to, one dose (one ml of desiccated vaccine dissolved in 1 ml of diluent) at birth, with three successive doses (each dose comprising one ml of desiccated vaccine dissolved in 1 ml of diluent) at monthly intervals, followed by annual booster vaccinations of the same dosage.

A schedule of vaccination involving one dose at birth, with further doses at intervals of one week for four weeks gave very good success.

Direct introduction of the vaccine into the respiratory tract, as for example, by intra-nasal introduction by nasal spray is particularly useful to treat animals suffering from respiratory involvement induced by the chlamydia organisms. This mode of immunization and treatment may be used alone or in conjunction with other therapy for the respiratory ailment.

Illustrative of the applicant's invention is the use of the vaccine to treat animals in a dairy herd. Calves were innoculated at birth using 1 cc dose of the vaccine in desiccated form and containing $10^{5.1}$ modified live organisms and dissolved in 1 cc of diluent (distilled water) and injected in the muscle of the calves, followed by three additional doses of the same potency and constituency at monthly intervals. Successful immunization against the Chlamydial organism resulted. Calves rather than adult animals were chosen for the initial experiment in order to obtain an early indication of possible toxic affects of the vaccine, since calves would be more susceptible to toxicity. Since there were no untoward problems associated with the vaccine in innoculating successively born calves in this first herd to be innoculated, the safety and effectiveness of the vaccine was further demonstrated by subsequently vaccinating over 2,000 calves from hundreds of dairy herds using the same dosage for each injection and injecting at the same, as well as at different intervals of time.

Not by way of limitation, but as shown in greater detail the use of applicant's invention, the following experiments are representative of the results achieved.

EXAMPLE I

A herd of dairy cattle in the State of Wisconsin, known to be infected with the Chlamydia organism after laboratory confirmation, had suffered severe problems for many years, including abortions, pneumonia, encephalomegaly, arthritis, serositis and neonatal diarrhea. Following the death of six consecutive neonatal calves due to pneumonia and/or enteritis during the late summer and early fall, the applicant commenced intramuscularly innoculating all calves the day they were born with the aforementioned Feline Pneumonitis Vaccine initially using a 1 cc dose of vaccine dissolved in 1 cc of diluent, following by three additional doses of the same potency and constituency at monthly intervals. Within approximately one year from the commencement of the vaccination program, 34 calves had been born in this herd and were vaccinated as explained above. Of the 34 calves vaccinated, only three calves died; one from pneumonia, one from congenital deformity, and one because of premature birth as a twin. In connection with EXAMPLE I, the applicant observed clinical evidence that the calves in this herd were in all probability born with a greater or lesser degree of Chlamydial infection and the symptoms thereof increased rapidly during the first 24 to 96 hours after birth. The vaccinated calves, except the three which died, fully recovered from the infection.

EXAMPLE II

A herd of Montana beef cows consisting of 300 stock cows were clinically diagnosed in the spring as suffering from a Chlamydial infection which appeared specifically as pneumonia accompanied by diarrhea in 20 calves approximately eight weeks of age. Of these 20 calves, the calves were selected at random, and were given intramuscular vaccinations with the aforementioned Feline Pneumonitis Vaccine of the aforementioned dosage weekly, for a total of four doses. After the first vaccination there were no observable changes. However, within 24 hours after the second vaccination, the diarrhea ceased, and the pneumonia symptoms remarkably improved during the first week. After the fourth vaccination, it was not possible to differentiate the ten vaccinated calves from calves that had never been ill. Four of the ten calves selected at random were initially very ill, and were expected to die. However, these four calves all completely recovered. The ten unvaccinated calves of the original 20 calves became stunted and never grew properly.

EXAMPLE III

Two young adult dairy cows in a Wisconsin herd suffered from a long-standing lameness due to swollen posterior, hock, and carpal joints. This lameness was clinically diagnosed as *Chlamydia psittaci* infection. In spring, after one intramuscular injection of the aforementioned Feline Pneumonitis Vaccine of the aforementioned dosage, following by another similar injection ten days later, both cows showed complete recovery from the lameness within fourteen days of this second injection and have shown no further symptoms.

EXAMPLE IV

In summer, two young adult dairy cows in a Wisconsin herd suffered from chronic bronchitis with frequent dry coughs which was diagnosed as *Chlamydia psittaci* infection. An intramuscular injection of the aforementioned Feline Pneumonitis Vaccine of the aforementioned disage was given, followed by a second such injection ten days later. Complete recovery from the coughing appeared within 48 hours following the second injection. However, there was a relapse within one week after the last injection, but with coughing of less frequency and severity and no further treatment followed. However, these animals were observed shortly before the time of filing of this application and were found to be remaining stable in view of the fact that they had suffered permanent lung damage.

EXAMPLE V

In summer, a herd of 120 veal calves two weeks old were vaccinated once for Infectious Bovine Rhinotrackeitis, Bovine Virus Diarrhea, and Para influenza-3. Sixty of these calves were also vaccinated once with the aforementioned Feline Pneumonitis Vaccine of the aforementioned dosage. The herd attendant was not told which calves were vaccinated with the Feline Pneumonitis Vaccine and four weeks later, when the herd was examined by applicant, the attendant stated there were fewer respiratory and enteric problems in sixty calves, which calves were then determined to be those that also had received the Feline Pneumonitis Vaccine. These calves were then clinically examined by the applicant and the noted improvements were verified.

EXAMPLE VI

In the fall, four calves, ten weeks old were suffering from chronic pneumonia. These calves were from a Wisconsin dairy herd known by laboratory confirmation to be infected with the Chlamydia organism. All four calves were given one dose of the aforementioned Feline Pneumonitis Vaccine intramuscularly. All four calves showed complete remission of symptoms in 72 hours. No further symptoms of disease developed in these calves.

EXAMPLE VII

In the summer, a two year old heifer from a Wisconsin herd known by laboratory confirmation to be infected with the Chlamydia organism developed moderate central nervous symptoms fourteen days before she was due to calve. These symptoms included loss of appetite and general lethargy. After she calved the symptoms became more aggravated and treatment was instituted, on the third day, post partum using accepted chemotherapeutic agents. She was completely unresponsive to this treatment over several days. Ten days after she calved, she was given one dose of the aforementioned Feline Pneumonitis Vaccine intramuscularly. In twenty-four hours, she was completely asymptomatic and has remained so.

EXAMPLE VIII

In the summer, a calf was born in a Wisconsin dairy herd known by laboratory confirmation to be infected with the Chlamydia organism. Severe lacramation, and front leg joint swelling were noted. The calf was given one dose of the aforementioned Feline Pneumonitis Vaccine intramuscularly and no other treatment was given. In 24 hours the hyperlacramation ceased, in seven days the joints were normal, and the calf remained normal. 9n

I claim:

1. A method of immunizing and treating bovines against *chlamydia psittaci* which comprises parenterally administering modified live Chlamydia feline pneumonitis vaccine to the bovines to stimulate the production of antibodies therein.

2. The method according to claim 1, wherein the vaccine is a modified live chlamydia vaccine of chicken embryo origin.

3. The method according to claim 2 wherein at least 1 ml of vaccine is administered.

4. The method according to claim 3 wherein the vaccine is administered intramuscularly.

5. The method according to claim 2 wherein at least 1 ml of the vaccine is administered followed by a second administration of at least 1 ml of the vaccine about ten days later.

6. The method according to claim 2 wherein at least 1 ml of the vaccine is administered followed by three successive administrations of at least 1 ml of the vaccine at one month intervals.

7. The method according to claim 5 wherein the vaccine is administered intramuscularly.

8. The method according to claim 6 wherein vaccine is administered intramuscularly.

9. A method of immunizing and treating an animal of the bovine species against *chlamydia psittaci* which comprises parenterally administering modified live chlamydia feline pneumonitis vaccine to said bovine to stimulate the production of antibodies comparable to those produced by natural infections when parenterally introduced into a non-immune animal of the same species without introducing the usual pathological symptoms of disease due to *chlamydia psittaci*.

10. The method according to claim 9 wherein the vaccine is administered intramuscularly.

11. The method according to claim 10 wherein at least 1 ml of the vaccine is so administered.

12. The method according to claim 10 wherein at least 1 ml of the vaccine is administered followed by administration of at least 1 ml of the vaccine about ten days later.

13. The method according to claim 10 wherein at least 1 ml of the vaccine is administered followed by three successive administrations of at least 1 ml of the vaccine at one month intervals.

14. A method of immunizing and treating bovines against *chlamydia psittaci* which comprises administering by the respiratory route modified live chlamydia feline pneumonitis, vaccine to the bovines to stimulate the production of antibodies therein.

15. A method of immunizing and treating an animal of the bovine species against *chlamydia psittaci* which comprises administering by the respiratory route modified live chlamydia feline pneumonitis vaccine to said bovine to stimulate the production of antibodies comparable to those produced by natural infections when parenterally introduced into a non-immune animal of the same species without introducing the usual pathological symptoms of diseases due to *chlamydia psittaci*.

16. The method set forth in claim 9 wherein said chlamydia vaccine is of chicken embryo origin.

17. The method set forth in claim 15 wherein said chlamydia vaccine is of chicken embryo origin.

* * * * *